(12) United States Patent
Nardi et al.

(10) Patent No.: US 7,842,840 B2
(45) Date of Patent: Nov. 30, 2010

(54) PROCESS FOR THE PREPARATION OF TRANS-2,3-DISUBSTITUTED NAPHTHOQUINONES

(75) Inventors: Antonio Nardi, Paderno Dungnano (IT); Mara Sada, Rho (IT); Annibale Salvi, Milan (IT); Stefano Maiorana, Milan (IT)

(73) Assignee: Laboratorio Chimico Internazionale, S.p.A., Milan (IT)

( * ) Notice: Subject to any disclaimer, the term of this patent is extended or adjusted under 35 U.S.C. 154(b) by 0 days.

(21) Appl. No.: 12/599,043

(22) PCT Filed: May 6, 2008

(86) PCT No.: PCT/IB2008/001110

§ 371 (c)(1),
(2), (4) Date: Dec. 9, 2009

(87) PCT Pub. No.: WO2008/139290

PCT Pub. Date: Nov. 20, 2008

(65) Prior Publication Data

US 2010/0137644 A1    Jun. 3, 2010

(30) Foreign Application Priority Data

May 9, 2007  (IT) .................. MI2007A0941

(51) Int. Cl.
*C07C 45/61* (2006.01)
(52) U.S. Cl. ...................................... 568/315
(58) Field of Classification Search .................. 568/315
See application file for complete search history.

(56) References Cited

U.S. PATENT DOCUMENTS 6,291,488 B1    9/2001    Gutteridge et al.

FOREIGN PATENT DOCUMENTS

EP    007551 A2    4/1983
EP    0123238 A2    10/1984

*Primary Examiner*—Sikarl A Witherspoon
(74) *Attorney, Agent, or Firm*—Lonnie Drayer

(57) ABSTRACT

The invention concerns a new process for the preparation of naphthoquinones, in particular an improved process for the preparation of 2,3-disubstituted 1,4-naphthoquinones, in the trans configuration.

22 Claims, No Drawings

PROCESS FOR THE PREPARATION OF TRANS-2,3-DISUBSTITUTED NAPHTHOQUINONES

CROSS REFERENCE TO RELATED APPLICATIONS

This is a 371 U.S. National Stage of International Application No. PCT/IB2008/001110, filed May 6, 2008, and published in English as WO 2008/139290 A1 on Nov. 20, 2008 the entire contents of which are incorporated herein by reference. PCT/IB2008/001110 claims priority of Italian patent application number MI2007A000941 filed May 9, 2007.

FIELD OF THE INVENTION

The present invention relates to a new process for the preparation of naphthoquinones, in particular a process for the preparation of 2,3-disubstituted 1,4-naphthoquinones, in the trans configuration.

2,3-trans-disubstituted 1,4-naphthoquinones are known as therapeutic agents. EP 77551 and EP 123238 describe 2,3-disubstituted 1,4-naphthoquinones, in particular 2-(cyclohexyl-substituted)-3-hydroxy in trans configuration which are prepared by epimerization of the corresponding cis/trans mixture. EP 77551 describes in particular the epimerization with concentrated sulfuric acid at 50-70° C. over a period ranging from 6 hours to several days. In example 5, EP 77551 reports the results of some epimerization reactions conducted on the derivative 2-(4-terbutyl-cyclohexyl)-3-hydroxy, at 50° C., 56° C. and 70° C. over a period ranging from 4 hours to 4 days; the cis/trans ratio obtained is specified but not the reaction yields.

The present inventors have ascertained that the above-described reactions result in a considerable degradation of the product and the corresponding yields of the required product are consequently very low.

OBJECT OF THE INVENTION

The object of the present invention is to provide an improved process for the preparation of 2-(cyclohexyl-substituted)-3-hydroxy disubstituted 1,4-naphthoquinones, in the trans configuration, which allows higher yields to be obtained.

This and further objects of the present invention will be described in detail below.

DETAILED DESCRIPTION OF THE INVENTION

Thus, according to one of its aspects, the present invention concerns a process for the preparation of a compound of formula (I) in the trans configuration

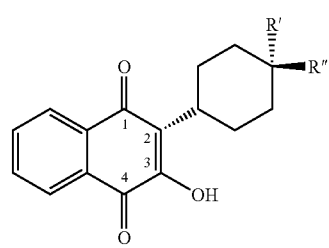

(I)

wherein R' is hydrogen and R" is selected from hydrogen $C_{1-6}$-alkyl, $C_{1-6}$-alkoxy, aryl-$C_{1-6}$-alkoxy, $C_{1-6}$-alkyl-$C_{1-6}$-alkoxy, halogen, perhalo-$C_{1-6}$-alkyl and phenyl optionally substituted with one or two groups chosen from atoms of halogen and $C_{1-6}$-alkyl, which comprises reacting a compound of formula (II), in the cis form or as a cis/trans mixture,

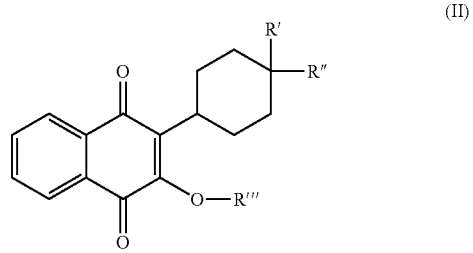

(II)

wherein R' and R" are as defined above, and R'" is an atom of hydrogen or a Pr protecting group hydrolysable in an acid environment with concentrated sulfuric acid at a temperature below +20° C.

According to the present invention, the term "$C_{1-6}$-alkyl" designates a linear or branched alkyl, containing from 1 to 6 atoms of carbon, for example methyl, ethyl, propyl, t-butyl, etc.

According to the present invention, the term "$C_{1-6}$-alcoxy" designates a linear or branched alkoxyl, containing from 1 to 6 atoms of carbon.

According to the present invention, the term "halogen" designates a halogen chosen from chlorine, bromine, fluorine or iodine, the chlorine being preferred.

According to the present invention, the term "perhalo" indicates the substitution of all the atoms of hydrogen of the alkyl group with atoms of halogen.

As "compound of formula (I) in the trans configuration" it is intended that the substituents in positions 1 and 4 of the cyclohexyl, i.e. the naphthoquinone substituent and R" are in the trans configuration.

As "compound of formula (I) in the cis configuration" it is intended that the substituents in positions 1 and 4 of the cyclohexyl, i.e. the naphthoquinone substituent and R" are in the cis configuration.

As "cis/trans mixture" it is intended that a mixture of compounds in the cis and trans configuration, as defined above, is present, in any relative ratio.

As a consequence, the expression "compound of formula (II), in cis form or in a cis/trans mixture" indicates, according to the present invention, that the starting compound of formula (II) is used as a pure cis conformer or as a mixture of cis/trans conformers in any relative ratio.

According to a preferred aspect, R" is a phenyl group, optionally substituted with an atom of halogen.

According to a particularly preferred aspect, R" is a 4-chloro-phenyl group.

The compound of formula (I) thus defined is a compound commercially available and is known under the INN "atovaquone".

According to another preferred embodiment, R" is a tert-butyl group. The compound of formula (I) thus defined is a compound commercially available and is known under the INN "buparvaquone".

The Pr hydrolysable protecting group is a protecting group of the hydroxy function which can be hydrolysed in an acid environment and is preferably chosen from the acrylic groups, whether aliphatic or aromatic, for example an acetyl, a benzoyl, etc.

A preferred Pr group is the acetyl group.

The term "concentrated sulfuric acid" here defines a sulfuric acid having a titer above 90%, for example equal to or higher than 96%.

According to the present invention, the expression "at a temperature below ambient temperature" indicates a temperature below +20° C. preferably below +15° C.

Advantageously the reaction is conducted at a temperature between −10° C. and +10° C., for example between 0° C. and +5° C.

Even when not explicitly indicated, when the sign "−" is not present, the temperatures are above zero according to the present invention.

In practice, the concentrated sulfuric acid is cooled to the chosen reaction temperature and the compound of formula (II) is slowly added, maintaining the temperature below +20° C.

The compound of formula (II)/concentrated sulfuric acid proportions are not critical and are preferably between ½ and ¹⁄₄₀ (p/w), advantageously between ¹⁄₁₀ and ¹⁄₂₀, for example approximately ¹⁄₁₈.

Contrarily to the teachings of the prior art referred to previously, it has been observed that the reaction is complete in a short time, sometimes in only approximately thirty minutes. A person skilled in the art can follow the course of the reaction by means of the known methods, verifying the disappearance of the cis isomer.

Thus, combining a low temperature with a shorter reaction duration, particularly advantageous reaction yields can be obtained, especially when compared with the yields obtained according to the known art. In the experimental section of the present description, comparative examples are given to demonstrate the significant improvements of the present invention with respect to the processes of the prior art.

As mentioned, said epimerization reaction must be conducted at temperatures below 20° C., advantageously below +15° C., to prevent the formation of excessive reaction by-products.

The experimental section of the present description provides the details of the comparative reactions conducted to verify the progress of and yields obtained by the epimerization reactions at temperatures above ambient temperature and direct alkylation of the non hydroxy-protected lawsone. The comparative examples confirm that the process of the invention offers the important advantages described above.

The compound of formula (I) in trans form thus obtained can be isolated and purified according to the methods known in the art, for example by extraction from the reaction environment in an appropriate solvent and purification by crystallization or chromatography column. Operating examples are provided in the following experimental section.

The compound of formula (II) in cis or cis/trans form can be prepared according to the methods known in the art, starting from hydroxy-protected lawsone (2-hydroxy-1,4-naphthoquinone), preferably as also described in EP 77551 and EP 123238.

According to another of its aspects, the invention concerns a process which comprises:

(a) reacting a compound of formula (III)

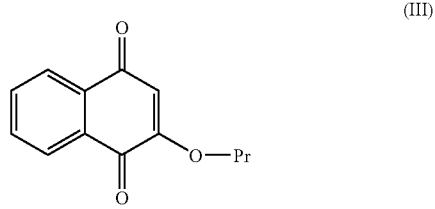

(III)

in which Pr is as defined above, with a group of formula (IV)

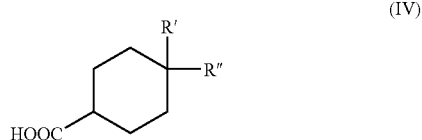

(IV)

in which R' and R" are as defined above, in conditions of radical oxidative coupling, for example in the presence of silver nitrate and ammonium persulfate;

(b) performing an epimerization reaction as defined above on the compound of formula (II), in which R''' is a Pr group thus obtained.

It appears clear that another important advantage of the present epimerization reaction with respect to the prior art derives from the observation that it is not necessary to eliminate the hydroxy protecting group, essential for correct performance of the reaction of phase (a) as above, before proceeding with the epimerization. As said, the epimerization step is successfully performed also in the presence of the Pr protecting group which, moreover, is eliminated simultaneously with the epimerization.

This important characteristic of the invention had never been taken into consideration in the prior art documents which, on the contrary, specified that hydrolysis of any protecting group present should be performed before proceeding with the epimerization.

The present invention therefore offers a double advantage as it permits the elimination of a synthesis step and, as a consequence of the elimination of said step, i.e. epimerizing the protected hydroxyl group, it provides a superior reaction yield.

The processes of the invention are particularly useful for the preparation of atovaquone and buparvaquone.

EXPERIMENTAL SECTION

Example 1

Preparation of the 2-Acetoxy-1,4-naphthoquinone (Acetyl-Lawsone)

595 g (5.89 moles) of triethylamine are added dropwise in 30 minutes to a suspension of 500 g (2.87 moles) of 2-hydroxy-1,4-naphthoquinone (lawsone) in 2200 ml of ethyl acetate, cooled to +5° C., maintaining the temperature below +10° C. At the end of the dripping a dark red solution is obtained. The solution is kept at +5-10° C. for 30 minutes. 550 g (5.39 moles) of acetic anhydride are added dropwise in 30 minutes, maintaining the temperature between +5 and +10° C. At the end of the dripping, the mixture is left under agitation at +5° C. for 4 hours. The solid is filtered and washed with a mixture of 250 ml of ethyl acetate and 250 ml of hexane pre-cooled to +5° C. The damp product is dried at +40° C. at reduced pressure for 6 hours providing 496 g (yield 80%) of 2-acetoxy-1,4-naphthoquinone (acetyl-lawsone) as a yellow solid with melting point −131°-134° C.

Example 2

Preparation of the 2-[4-(p-chlorophenyl)-cyclo-hexyl]-3-acetoxy-1,4-naphthoquinone (CIS/TRANS acetyl-atovaquone)

100 g (0.46 moles) of 2-acetoxy-1,4-naphthoquinone and 88.4 g (0.37 moles) of 4-(4-chlorophenyl)-cyclohexanecarboxylic acid are added to 560 ml of acetonitrile. The mixture is left under agitation at 20-25° C. for 10 minutes. A solution of 20.4 g (0.12 moles) of silver nitrate in 133 ml of deionised water is added. The mixture is heated to reflux temperature (78-80° C.); a solution of 179 g (0.8 moles) of ammonium persulfate in 600 ml of deionised water is added dropwise in approximately 1 hour. At the end of the dripping, the mixture is left under agitation for 2 hours at reflux temperature. It is cooled to 70° C., 1000 ml of toluene are added and the mixture is left under agitation at 60-70° C. for 10 minutes. The phases are separated and the organic phase is washed three times with 500 ml of water for each wash. The organic phase is filtered and concentrated to ⅓ of the initial volume by distillation of the toluene at reduced pressure. It is cooled to 20-25° C. and left under agitation for 12-14 hours; the temperature is then brought to 0-5° C. and maintained for 1 hour. The solid is filtered and washed with 20 ml of toluene pre-cooled to +5° C. and then with 20 ml of acetone. The damp product is dried at 40° C. for 6-8 hours, providing 44 g of acetyl-atovaquone mainly in the CIS configuration (melting point 197-200° C.). 400 ml of acetone are added to the crystallisation mother liquor and the mixture is left under agitation at 20-25° C. for 16 hours. It is cooled to 0-5° C. and left at said temperature for 2 hours. The solid is filtered and washed with 10 ml of acetone pre-cooled to 5° C. The damp product is dried at 40° C. for 6-8 hours providing 19 g of acetyl-atovaquone mainly in the TRANS configuration (melting point 150-155° C.). The two dried solids are re-combined to give 63 g of CIS/TRANS acetyl-atovaquone (yield 41.7%).

Example 3

Preparation of the 2-[trans-4-(p-chlorophenyl)-cyclo-hexyl]-3-hydroxy-1,4-naphthoquinone (atovaquone) by epimerization and deprotection of the CIS/TRANS acetyl-atovaquone with concentrated sulfuric acid at 0-5° C.

20 g (48.9 mmoles) of CIS/TRANS acetyl-atovaquone are added portionwise in 15 minutes to 200 ml of sulfuric acid 96% pre-cooled to 0° C. During the addition the internal temperature is maintained at 0-5° C. At the end of the addition it is left under agitation at 0-5° C. for 30 minutes and the temperature is then left to rise spontaneously to 20-25° C. The reaction mixture is poured slowly onto 500 ml of water pre-cooled to +5° C. without exceeding the internal temperature of 25° C. 600 ml of methyl ethyl ketone are added and the mixture is heated to 60° C. The acid aqueous phase is separated and the organic phase is washed with 100 ml of water, maintaining the temperature at 50-60° C. The organic phase is concentrated to approximately half the initial volume by distillation of the solvent at atmospheric pressure. It is gradually cooled to 0-5° C. and maintained cold for 1 hour. The solid is filtered and washed with 20 ml of cold methyl ethyl ketone. The damp product is dried at 45° C. at reduced pressure for 6-8 hours providing 12 g of atovaquone (yield 67%). The raw product is purified by crystallisation from 180 ml of methyl ethyl ketone obtaining an atovaquone having a melting point of 220-223° C.

HPLC purity: >99%

1H-NMR (CDCl3, 300 MHz): δ=1.5-2.3 (8H, m); 2.67 (1H, m); 3.2 (1H, m); 7.2-8.2 (8H, m)

Example 4

Preparation of the Atovaquone by Epimerization and Deprotection of the CIS/TRANS Acetyl-Atovaquone with Concentrated Sulfuric Acid at +15° C.

8 g (19.6 mmoles) of CIS/TRANS acetyl-atovaquone are added portionwise in 15 minutes to 80 ml of sulfuric acid 96% at +15° C. At the end of the addition it is left under agitation at 15° C. for 30 minutes and the temperature is then brought to 20-25° C. The reaction mixture is poured slowly onto 230 ml of water pre-cooled to 5° C. without exceeding the internal temperature of 25° C. 160 ml of toluene are added and the mixture is heated to 70° C. The acid aqueous phase is separated and the organic phase is washed with a solution of 8 g of sodium chloride in 40 ml of water, maintaining the temperature at 60° C. The organic phase is concentrated to approximately ⅓ of the initial volume by distillation of the solvent at atmospheric pressure. It is gradually cooled to 0-5° C. and maintained cool for 1 hour. The solid is filtered and washed with 10 ml of cold toluene. The damp product is dried at 45° C. at reduced pressure for 6-8 hours, providing 6.08 g of atovaquone (yield 76%) with HPLC purity >99%.

Example 5

Preparation of the Atovaquone by Epimerization of the Cis/Trans Atovaquone with Concentrated Sulfuric Acid at +5° C.

8 g (21.8 mmoles) of CIS/TRANS atovaquone in a ratio of 58/42 are added portionwise in 15 minutes to 80 ml of sulfuric acid 96% at +5° C. At the end of the addition it is left under agitation at 5° C. for 30 minutes and the temperature is then brought to 20-25° C. The reaction mixture is poured slowly onto 230 ml of water pre-cooled to 5° C. without exceeding the internal temperature of 25° C. 340 ml of methyl ethyl ketone are added and the mixture is heated to 70° C. The acid aqueous phase is separated and the organic phase is washed with a solution of 8 g of sodium chloride in 80 ml of water, maintaining the temperature at 60° C. The organic phase is concentrated to approximately ⅙ of the initial volume by distillation of the solvent at atmospheric pressure. It is gradually cooled to 0-5° C. and maintained cold for 1 hour. The solid is filtered and washed with 10 ml of water. The damp product is dried at 45° C. at reduced pressure for 6-8 hours, providing 6.5 g of atovaquone (yield 81%) with HPLC purity >99% (CIS isomer=0.45%).

Example 6

Comparative

Preparation of the Atovaquone by Epimerization and Deprotection of the CIS/TRANS Acetyl-Atovaquone with Concentrated Sulfuric Acid at 50° C.

Operating as described in example 4 but performing the epimerization reaction at 50° C. instead of at 15° C., 1.8 g of atovaquone (yield 25%) are obtained.

Example 7

Comparative

Preparation of the 2-[4-(p-chlorophenyl)-cyclohexyl]-3-hydroxy-1,4-naphthoquinone (cis/trans atovaquone) starting from the 2-hydroxy-1,4-naphthoquinone 10 g (57 mmoles) of 2-hydroxy-1,4-naphthoquinone, 20.5 g (85.9 mmoles) of 4-(4-chlorophenyl)-cyclohexanecarboxylic acid and 6 g (35 mmoles) of silver nitrate are added to 150 ml of acetonitrile and 150 ml of water. The mixture is heated to reflux temperature (75-80° C.) and a solution of 18 g (79 mmoles) of ammonium persulfate in 100 ml of deionised water is then added dropwise in approximately 1 hour. At the end of the dripping, it is left under agitation for 2 hours at reflux temperature. The reaction mixture is sampled and the HPLC analysis highlights a very low conversion (5-10%) with significant formation of by-products. A further 9 g of ammonium persulfate and 3 g of silver nitrate are added and left at reflux for a further 4 hours. The mixture is sampled again but the HPLC analysis does not highlight any substantial change in the previous situation: conversion approximately 10% and presence of by-products.

What is claimed is:

1. A process for the preparation of a compound of formula (I)

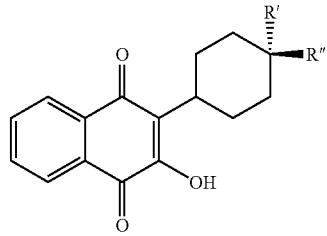

(I)

wherein R' is hydrogen and R" is selected from hydrogen $C_{1-6}$-alkyl, $C_{1-6}$-alkoxy, aryl-$C_{1-6}$-alkoxy, $C_{1-6}$-alkyl-$C_{1-6}$-alkoxy, halogen, perhalo-$C_{1-6}$-alkyl, phenyl optionally substituted with one or two groups chosen from atoms of halogen and $C_{1-6}$-alkyl, which comprises reacting a compound of formula (II), in cis form or as a cis/trans mixture,

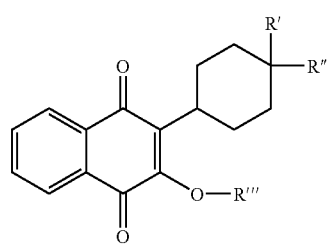

(II)

wherein
R' and R" are as defined above, and
R'" is an atom of hydrogen or a Pr protecting group hydrolysable in an acid environment, with concentrated sulfuric acid, at a temperature below +20° C.

2. The process as claimed in claim 1, wherein R" is a 4-chloro-phenyl group.

3. The process as claimed in claim 1, wherein R" is a tert-butyl group.

4. The process as claimed in claim 1, wherein R'" is Pr.

5. The process as claimed in claim 1, wherein R'" is Pr, and Pr is an acetyl group.

6. The process as claimed in claim 1, wherein the reaction is performed at a temperature below +15° C.

7. The process as claimed in claim 1, wherein the reaction is performed at a temperature between −10° C. and +10° C.

8. The process as claimed in claim 1, wherein the reaction is performed at a temperature between 0° C. and +5° C.

9. The process as claimed in claim 1, wherein the compound of formula (II) as defined in claim 1 is prepared by reacting a compound of formula (III)

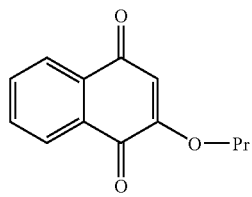

(III)

wherein Pr is either as defined in claim 1 or is an acetyl group, with a group of formula (IV)

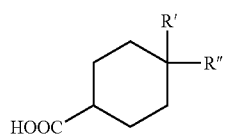

(IV)

wherein R' and R" are as defined in claim 1, in conditions of radical oxidative coupling.

10. The process as claimed in claim 9, wherein the oxidative coupling conditions are obtained in the presence of silver nitrate and ammonium persulfate.

11. The process as claimed in claim 9 for the preparation of atovaquone.

12. The process as claimed in claim 9 for the preparation of buparvaquone.

13. The process as claimed in claim 1, wherein R''' is Pr and the compound of formula (II) as defined in claim 1 is prepared by reacting a compound of formula (III)

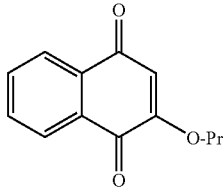
(III)

wherein Pr is either as defined in claim 1 or is an acetyl group, with a group of formula (IV)

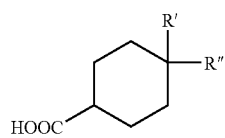
(IV)

wherein R' and R" are as defined in claim 1, in conditions of radical oxidative coupling.

14. The process as claimed in claim 6, wherein the compound of formula (II) is prepared by reacting a compound of formula (III)

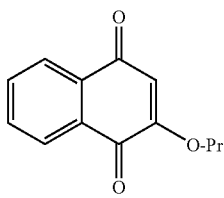
(III)

wherein Pr is either as defined in claim 1 or is an acetyl group, with a group of formula (IV)

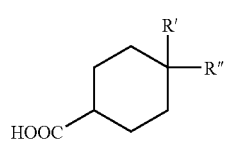
(IV)

wherein R' and R" are as defined in conditions of radical oxidative coupling.

15. The process as claimed in claim 7, wherein the compound of formula (II) is prepared by reacting a compound of formula (III)

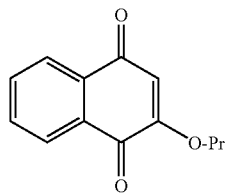
(III)

wherein Pr is either as defined or is an acetyl group, with a group of formula (IV)

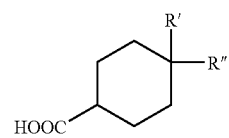
(IV)

wherein R' and R" are as defined in conditions of radical oxidative coupling.

16. The process as claimed in claim 8, wherein the compound of formula (II) is prepared by reacting a compound of formula (III)

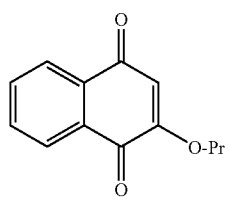
(III)

wherein Pr is either as defined or is an acetyl group, with a group of formula (IV)

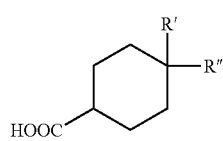
(IV)

wherein R' and R" are as defined in conditions of radical oxidative coupling.

17. The process as claimed in claim 10 for the preparation of atovaquone.

18. The process as claimed in claim 10 for the preparation of buparvaquone.

19. The process as claimed in claim 2, wherein R''' is Pr.

20. The process as claimed in claim 3, wherein R''' is Pr.

21. The process as claimed in claim 2, wherein R''' is Pr, and Pr is an acetyl group.

22. The process as claimed in claim 3, wherein R''' is Pr, and Pr is an acetyl group.

* * * * *